(12) United States Patent
Zhang et al.

(10) Patent No.: US 11,703,474 B2
(45) Date of Patent: Jul. 18, 2023

(54) METHOD FOR OPTIMIZING STRUCTURE OF ECT SENSOR AND ANALYZING ELECTROMAGNETIC FIELD

(71) Applicant: QINGDAO UNIVERSITY OF TECHNOLOGY, Shandong (CN)

(72) Inventors: Peng Zhang, Shandong (CN); Wentao Wang, Shandong (CN); Kaiyue Zhao, Shandong (CN); Jiuwen Bao, Shandong (CN); Tiejun Zhao, Shandong (CN)

(73) Assignee: QINGDAO UNIVERSITY OF TECHNOLOGY, Shandong (CN)

( * ) Notice: Subject to any disclaimer, the term of this patent is extended or adjusted under 35 U.S.C. 154(b) by 186 days.

(21) Appl. No.: 17/433,095

(22) PCT Filed: Nov. 26, 2020

(86) PCT No.: PCT/CN2020/131878
§ 371 (c)(1),
(2) Date: Aug. 23, 2021

(87) PCT Pub. No.: WO2021/189893
PCT Pub. Date: Sep. 30, 2021

(65) Prior Publication Data
US 2022/0341866 A1   Oct. 27, 2022

(30) Foreign Application Priority Data
Mar. 26, 2020 (CN) .......................... 202010222125.4

(51) Int. Cl.
*G01N 27/22* (2006.01)
*G01N 33/38* (2006.01)

(52) U.S. Cl.
CPC ......... *G01N 27/223* (2013.01); *G01N 27/226* (2013.01); *G01N 33/383* (2013.01)

(58) Field of Classification Search
CPC .. G01N 27/223; G01N 27/226; G01N 33/383; G01N 27/24; G01N 27/221
See application file for complete search history.

(56) References Cited

U.S. PATENT DOCUMENTS

2014/0361793 A1\* 12/2014 Marashdeh ........... G01F 1/7046
324/663
2016/0054247 A1\* 2/2016 Colosimo ............ G01N 27/026
324/629

(Continued)

*Primary Examiner* — Alvaro E Fortich
(74) *Attorney, Agent, or Firm* — Meunier Carlin & Curfman LLC

(57) ABSTRACT

The present application belongs to the technical field of monitoring of durability of concrete, and particularly relates to a method for optimizing a structure of an electrical capacitance tomography sensor and analyzing an electromagnetic field. A specific process of the method includes eight steps: parameter setting, geometric setting, material setting, mesh generation, physical field setting, solution, sensor structure optimization and calculation of electromagnetic field distribution. The method proposes a new concept for solving a forward problem of an ECT system based on COMSOL software. After modeling is completed, uniformity of a sensitive field of the ECT sensor is analyzed according to calculation results, and structural parameter values of components of the ECT sensor are adjusted to seek an optimal design scheme.

2 Claims, 2 Drawing Sheets

(56) References Cited

U.S. PATENT DOCUMENTS

| | | | |
|---|---|---|---|
| 2016/0091448 A1* | 3/2016 | Soleimani | G01N 27/22 324/654 |
| 2016/0340245 A1* | 11/2016 | Loh | C04B 20/1029 |
| 2019/0046104 A1* | 2/2019 | Samani | A61B 5/0536 |
| 2019/0202738 A1* | 7/2019 | Li | C04B 18/08 |

* cited by examiner

METHOD FOR OPTIMIZING STRUCTURE OF ECT SENSOR AND ANALYZING ELECTROMAGNETIC FIELD

CROSS-REFERENCE TO RELATED APPLICATIONS

This is a U.S. national application of the international application number PCT/CN2020/131878 filed on Nov. 26, 2020 claiming priority of Chinese Patent Application number 202010222125.4 filed on Mar. 6, 2020, the contents of both of which are incorporated herein by reference.

TECHNICAL FIELD

The present disclosure belongs to the technical field of monitoring durability of concrete, and particularly relates to a method for optimizing a structure of an electrical capacitance tomography (ECT) sensor and analyzing an electromagnetic field. The method may quickly solve a forward problem of imaging of an ECT sensor, and realize optimization of the structure of the ECT sensor as well as an accurate calculation and a rapid analysis of the electromagnetic field change in a measurement field.

BACKGROUND ART

Durability of a concrete structure has always been a hot topic in civil engineering, which is not only directly related to major issues such as saving of energy, saving of consumables and environmental protection, but also has a far-reaching influence on sustainable development of economy and society. Among many reasons for durability failure of the concrete structure, existence and migration of moisture are important inducements and key factors that cause lack of durability. On the one hand, the moisture is a carrier for a corrosive medium to enter the concrete, and on the other hand, the moisture is also a necessary condition for a deterioration reaction process. Therefore, it is of great significance to dynamically monitor and quantitatively analyze a moisture transmission process based on a visualization technology.

ECT is a non-destructive testing technology based on a capacitance sensitive mechanism, and has a working principle as follows: based on a fact that different substances have different dielectric constants, specially designed sensitive array sensors are adopted, and a distribution of a medium in a target field is constructed by using an appropriate image reconstruction algorithm and measuring voltages between sensitive electrodes, thereby realizing visual measurement of the distribution of the medium. The ECT technology has advantages of no invasion, fast response, wide application range, low cost, no radiation, portability, etc. Therefore, the ECT technology may be used to quantitatively study internal moisture distribution of the concrete structure, to provide an effective technical support for a more objective and accurate evaluation of the durability of the concrete structure.

An ECT system consists of three parts, including an array capacitance sensor, a data acquisition and information processing system and an imaging computer. Herein, the array capacitance sensor is a core of the ECT system. On the one hand, quality of an image reconstructed by ECT directly depends on uniformity of a sensitive field inside the sensor depending on a design of structural parameters; on the other hand, a forward problem of ECT imaging is to set a structure of a sensor, a measurement strategy between electrodes as well as a medium distribution in the sensitive field and to solve an electromagnetic field distribution in a field to finally obtain a corresponding relationship between a boundary response value and the medium distribution in the field. Therefore, for concrete component, designing and optimizing a corresponding structure of the sensor and accurately calculating the electromagnetic field distribution in the field are important preconditions for quantitatively monitoring moisture content in the concrete component.

A macro electromagnetic field phenomenon in a measurement field of an ECT sensor may be expressed by the Maxwell equation set:

$$\begin{cases} \nabla \times H = J + \dfrac{\partial D}{\partial t} \\ \nabla \times E = -\dfrac{\partial B}{\partial t} \\ \nabla \cdot B = 0 \\ \nabla \cdot D = \rho \end{cases},$$

where a magnetic field intensity H, an electric field intensity E, a magnetic induction intensity B and an electric flux density D are four field vectors, and a current density J and a charge density $\rho$ are two source variables.

When a measurement region of the ECT system is a linear and isotropic homogeneous medium, there exists a constitutive relationship as follows:

$$\begin{cases} D = \varepsilon E \\ B = \mu H, \\ J = \sigma E \end{cases}$$

when a working frequency of an excitation power supply is within a low frequency band, the excitation power supply meets requirements of an electrostatic field, and a fundamental equation of the electrostatic field is as follows:

$$\begin{cases} D = \varepsilon E \\ \nabla \cdot D = 0 \\ E = -\nabla \phi, \\ \nabla \times E = 0 \end{cases}$$

where $\varepsilon$ represents a dielectric constant, $\mu$ represents magnetic permeability and $\phi$ represents electric potential energy.

According to the above equation set, it can be concluded that a mathematical model of the ECT system is a Poisson equation:

$$\nabla \cdot (\varepsilon \cdot \nabla \phi) = 0$$

According to the Gaussian formula, capacitance between electrode pairs i and j for solving the forward problem is:

$$C_{i,j} = \frac{Q}{\varphi_i - \varphi_j} = \frac{\oiint_A \varepsilon(x,y)E dA}{\varphi_i - \varphi_j} = \frac{\oiint_A \varepsilon(x,y)\nabla \varphi(x,y) \cdot dA}{\varphi_i - \varphi_j}$$

where $\varphi_i - \varphi_j$ is a potential difference between an excitation electrode i and a measuring electrode j, A represents an area of a closed region of the electrode j, and Q represents a quantity of induced charges on the electrode j.

The above forward problem of the ECT may be solved by using an analytical method and a finite element analysis method. When the above formula is solved by using the analytical method, a derivation process is complicated, and an accurate field model needs to be established, so it is difficult to get an accurate solution. In contrast, when the finite element analysis method is adopted, a field to be solved is divided into a plurality of small units, a limited number of unknown elements are used to approach a real field with infinite unknown elements, and the finite element analysis method achieves high calculation accuracy and is suitable for solving various complicated fields. Therefore, forward problems of the ECT are mostly solved by using the finite element method. However, at present, most researches on the ECT sensors only focus on a visual monitoring of two-phase flow in pipelines, there are few patents about the ECT sensors related to the field of concrete, and there is even no relevant literature report about specific modeling and analysis methods for the ECT sensors.

An ECT technology based on capacitance measurement is quite sensitive to moisture in a cement-based material. Therefore, the ECT technology shows its unique advantages in quantitative monitoring of moisture distribution in the cement-based material. Through computer modeling and analysis, an internal structure of an ECT sensor applicable to the field of concrete is designed and optimized, an electromagnetic field distribution in a field where a concrete component is located in is calculated accurately and quickly, and actual test results are compared and analyzed, thereby providing a new research concept and means for durability problem of the concrete and realizing accurate prediction of the durability of a concrete structure.

SUMMARY

The present disclosure intends to overcome the shortcomings of the prior art and design a method for optimizing a structure of an ECT sensor and analyzing an electromagnetic field, thereby realizing design optimization of structural parameters of the sensor and an accurate calculation of an electromagnetic field distribution in a measurement field to provide a theoretical basis for quantitative and visual monitoring of moisture content in a concrete component.

In order to achieve the above effects, a specific process of the method for optimizing the structure of the ECT sensor and analyzing the electromagnetic field related to the present disclosure includes eight steps of parameter setting, geometric setting, material setting, mesh generation, physical field setting, solution, sensor structure optimization and calculation of electromagnetic field distribution:

(1) parameter setting: sequentially inputting parameter values of components in a real diagram of the ECT sensor in a COMSOL software (finite element analysis software) so as to change the parameter values quickly after modeling, and observing the electromagnetic field distribution in a measurement field 1 of the ECT sensor when different design parameter values are given;

where the parameter values include a radius of the measurement field 1 of the ECT sensor, a thickness of a PVC layer 2, a size and an opening angle of a copper electrode layer 3, an embedding depth of a radial electrode layer 4, a radius of an air field 5, a radius of a shielding layer 6 and a size of an impurity region 7;

(2) geometric setting: establishing a finite element model of the ECT sensor according to the real diagram in the COMSOL software, and sequentially establishing a concrete component, the PVC layer 2, the copper electrode layer 3, the radial electrode layer 4, the air field 5, the shielding layer 6 and the impurity region 7 in the measurement field 1 of the ECT sensor by taking a center of the finite element model of the ECT sensor as a center of a circle;

(3) material setting: setting a material of the measurement field 1 of the ECT sensor as concrete, setting a material of the PVC layer 2 as plastic, setting materials of the copper electrode layer 3 and the shielding layer 6 as copper, setting a material of the air field 5 as air, and setting material properties (relative dielectric constant, relative permeability, conductivity and density) of the impurity region 7 according to setting requirements;

(4) mesh generation: setting a category of a mesh generation of a region of the finite element model of the ECT sensor as free triangular mesh generation, and setting sizes of maximum and minimum unit meshes according to set accuracy to further improve calculation accuracy;

(5) physical field setting: sequentially setting 12 electrodes of the finite element model of the ECT sensor as terminals, and setting parametric scanning so that electrode plates are excited in turn in a measurement process; observing the electromagnetic field distribution under different excitation conditions; and setting an external shielding device to be grounded;

(6) solution: calculating a Maxwell capacitance matrix, a mutual inductance capacitance matrix and a sensitivity matrix in the COMSOL software, and sequentially drawing detailed data diagrams of an electric field, potential and sensitivity thereby preliminarily completing the calculation of the electromagnetic field distribution in the measurement field 1 of the ECT sensor;

(7) sensor structure optimization: introducing an optimization function by utilizing the sensitivity obtained in the solution step, and obtaining a set of optimal parameter values through a factor rotation design test method or an orthogonal optimization design method, to realize parameter optimization of the sensor structure, improve uniformity of a sensitive field, and obtain air ECT sensor with an optimized structure; and (8) calculation of electromagnetic field distribution: measuring relative dielectric constants of a concrete structure with different moisture contents through tests based on the electromagnetic field distribution in the measurement field 1 of the ECT sensor, and correspondingly changing a dielectric constant of the measurement field 1 of the ECT sensor in the finite element model of the ECT sensor to simulate a change of the electromagnetic field when the moisture content in the measurement field 1 of the ECT sensor changes to realize an accurate analysis of the electromagnetic field when the moisture content in the concrete structure changes, thereby better explaining test results and providing a theoretical basis for a durability analysis of the concrete structure.

The finite element model of the ECT sensor related to the present disclosure is two-dimensional; the concrete component in the measurement field 1 of the ECT sensor is a linear and isotropic medium; a measurement frequency is within a low frequency band; the measurement field 1 of the ECT sensor is set as an electrostatic field; and options of two-dimension, electrostatic module and stable state research are sequentially selected in the COMSOL software.

The ECT sensor related to the present disclosure is an ECT sensor disclosed in Chinese Patent 201910904259.1 for monitoring moisture transmission in the concrete component.

Compared with the conventional art, the present disclosure proposes a new concept and an analysis method for solving a forward problem of an ECT system based on the COMSOL software. Herein, the uniformity of the sensitive field of the ECT sensor is analyzed according to calculation results after modeling is completed; structural parameter values of components of the ECT sensor are adjusted to seek the best design scheme. Meanwhile, changes of an internal electromagnetic field due to the moisture contained the concrete structure may be observed directly and clearly to obtain a relationship between the internal moisture content and the relative dielectric constant of the concrete structure, thereby improving the accuracy of the moisture content in the concrete structure in an ECT imaging technology, providing a new verification method for a durability test of the concrete structure, and providing a new concept and a theoretical basis for durability analysis of the concrete structure. The method for optimizing the structure of the ECT sensor and analyzing the electromagnetic field has the following advantages: (1) a two-dimensional ECT sensor modeling analysis method is simple in operation, convenient in application and practical, and greatly reduces calculation time in comparison with a three-dimensional modeling analysis method; (2) the structure of the ECT sensor may be optimized quickly by adjusting the parameter values of the ECT sensor in the finite element model, thereby reducing non-uniformity characteristics of the sensitive field of the ECT sensor and improving measurement accuracy of the ECT sensor; (3) the forward problem in measurement of the ECT sensor may be solved quickly, thereby realizing an accurate calculation of the Maxwell capacitance matrix, the mutual inductance capacitance matrix and the sensitivity matrix in the measurement region 1 of the ECT sensor, to obtain the detailed data diagrams of the electric field, the potential and the sensitivity, and provide a theoretical basis for visual monitoring of the ECT sensor; (4) the COMSOL software is used to model and analyze the ECT sensor, which achieves a high test controllability, an accurate and fast calculation, direct and clear results, high real-time performance and a relatively high economic value, and assists in analyzing test results when the ECT system visually monitors the moisture content in the concrete structure; and (5) the finite element model of the ECT sensor may be verified by a simple test, thereby realizing comparison verification of imaging results under complex test conditions and solving a problem about lack of comparison verification of ECT imaging results of an existing concrete component.

DETAILED DESCRIPTION OF THE EMBODIMENTS

Figure 1:
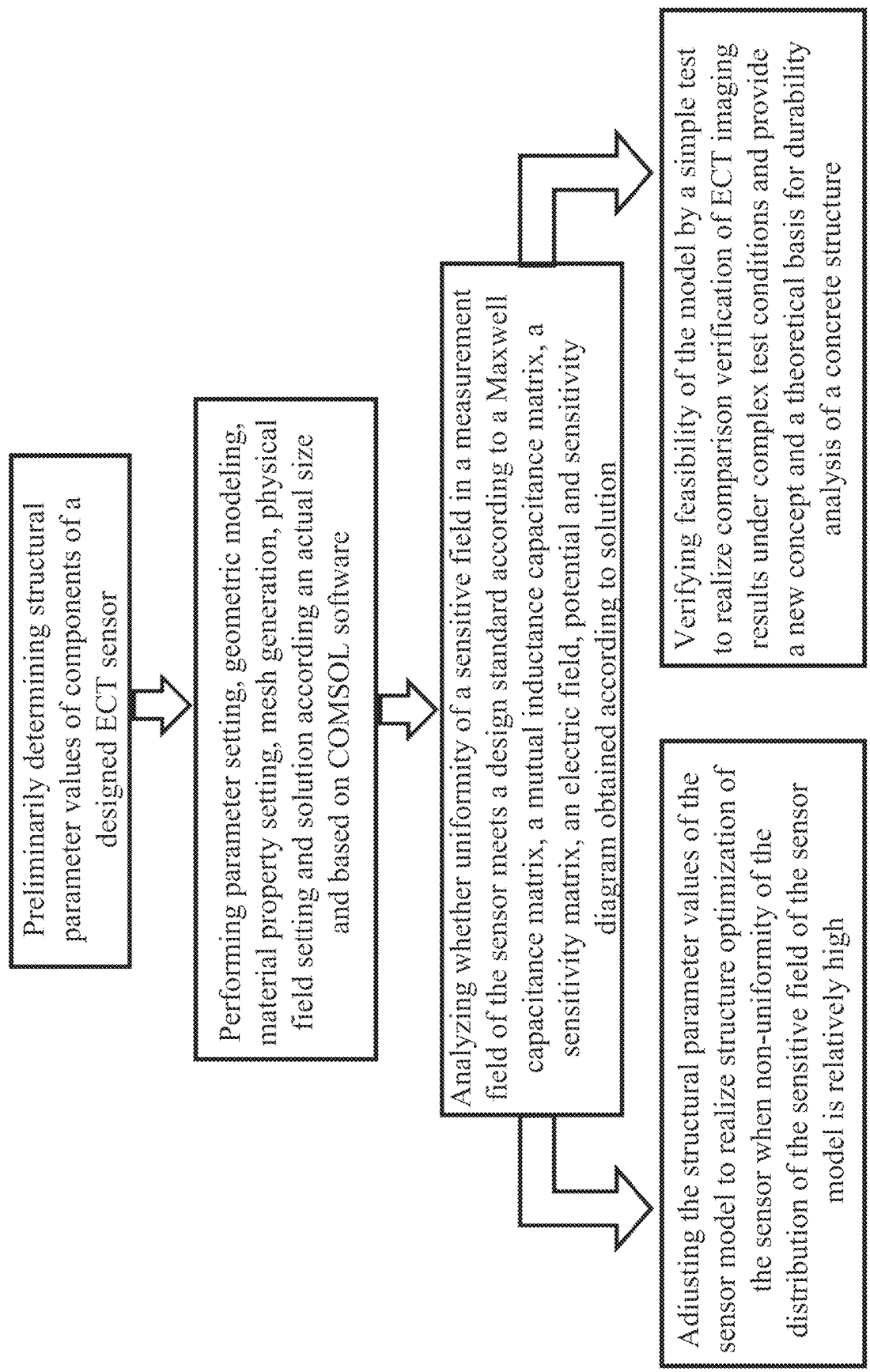
FIG. 1 is a process flowchart of the present disclosure.
Figure 2:
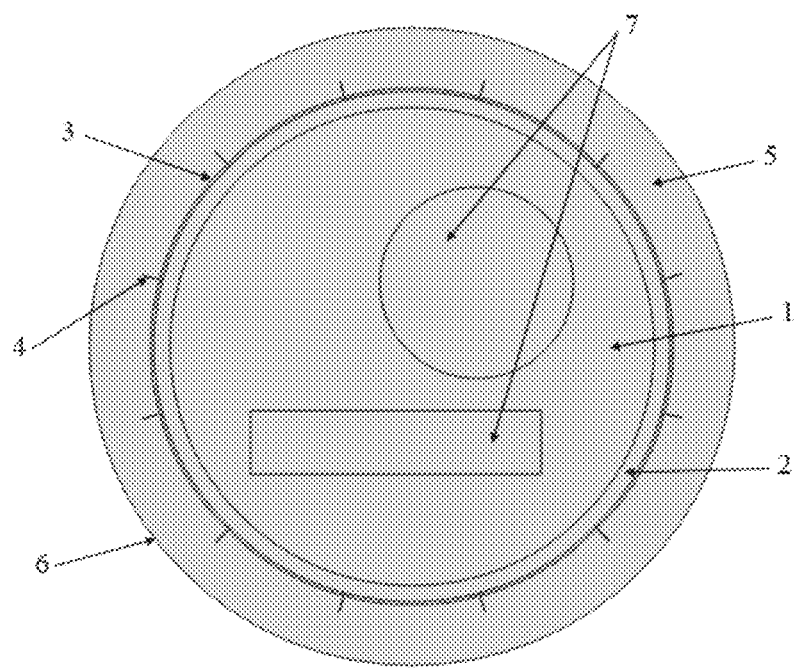
FIG. 2 is a schematic diagram of a finite element model of an ECT sensor of the present disclosure.
Figure 3:
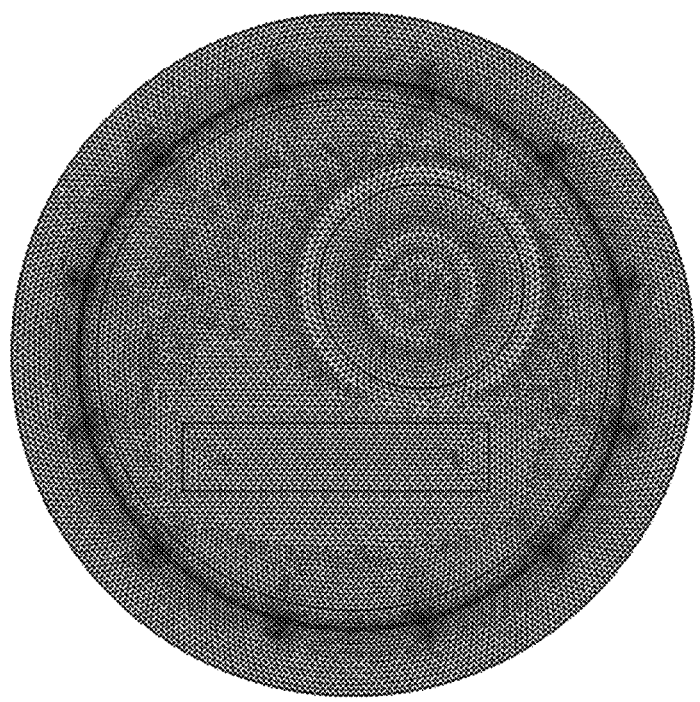
FIG. 3 is a schematic diagram of mesh generation of the finite element model of the ECT sensor of the present disclosure.

The present disclosure will be further described below through embodiments.

Embodiment 1

A specific process of a method for optimizing a structure of an ECT sensor and analyzing an electromagnetic field related to this embodiment includes eight steps: parameter setting, geometric setting, material setting, mesh generation, physical field setting, solution, sensor structure optimization and calculation of electromagnetic field distribution:

(1) parameter setting: parameter values of components in a real diagram of the ECT sensor are sequentially input in a global definition catalogue of the COMSOL software (finite element analysis software) so as to change the parameter values quickly after modeling and observe the electromagnetic field distribution in the measurement field 1 of the ECT sensor when different design parameter values are given. Herein, a radius of a measurement field 1 of the ECT sensor is 7.5 cm, a thickness of a PVC layer 2 is 0.5 cm, a width and an opening angle of a copper electrode layer 3 are 4 cm and $$\frac{180° \times \text{Electrode width}}{\text{outer diameter of PVC tube}}$$

respectively, a embedding depth of a radial electrode layer 4 is 0, a radius of an air field 5 is 10 cm, a radius of a shielding layer 6 is 10 cm, and an impurity region 7 is a moisture-containing region with a radius of 3 cm and a moisture-containing region of 10×2 cm.

(2) geometric setting: a finite element model of the ECT sensor is established according to the real diagram in the COMSOL software, and a concrete component, the PVC layer 2, the copper electrode layer 3, the radial electrode layer 4, the air field 5, the shielding layer 6 and the impurity region 7 in the measurement field 1 of the ECT sensor are sequentially established by taking a center of the finite element model of the ECT sensor as a center of a circle.

(3) material setting: a material of the measurement field 1 of the ECT sensor is set as concrete, a material of the PVC layer 2 is set as plastic, materials of the copper electrode layer 3 and the shielding layer 6 are set as copper, a material of the air field 5 is set as air, and material properties (relative dielectric constant, relative permeability, conductivity and density) of the impurity region 7 are set according to setting requirements.

(4) mesh generation: a category of a mesh generation of a region of the finite element model of the ECT sensor is set as free triangular mesh generation, and a size of the maximum unit mesh is set to be 2 mm and a size of the minimum unit mesh is set to be 0.5 mm according to set accuracy to further improve calculation accuracy.

(5) physical field setting: 12 electrodes of the finite element model of the ECT sensor are sequentially set as terminals, an excitation voltage is set to be 5 V, and parametric scanning is set so that electrode plates may be excited in turn in a measurement process to observe the electromagnetic field distribution under different excitation conditions; and an external shielding device is set to be grounded.

(6) solution: a Maxwell capacitance matrix, a mutual inductance capacitance matrix and a sensitivity matrix are calculated in the COMSOL software, and detailed data diagrams of an electric field, potential and sensitivity are sequentially drawn, thereby preliminarily completing the calculation of the electromagnetic field distribution in the measurement field 1 of the ECT sensor.

(7) sensor structure optimization: an optimization function $$P = \frac{\sum_{i=1}^{12}\sum_{j=2}^{12}\left|\frac{S_{devi,j}}{S_{avgi,j}}\right|}{11}$$

is introduced by using the sensitivity $S_{i,j}(k)$ obtained in the solution step, $S_{avgi,j}$ and $S_{devi,j}$ are a mean value and a standard deviation of a sensitive field respectively. And a set of optimal parameter values is obtained through a factor rotation design test method or an orthogonal optimization design method to realize parameter optimization of the sensor structure, improve uniformity of the sensitive field, and obtain an ECT sensor with an optimized structure, where the optimal parameter values include the thickness of the PVC layer 2, the size of the copper electrode layer 3, and the embedding depth of the radial electrode layer 4.

(8) calculation of electromagnetic field distribution: relative dielectric constants of a concrete structure with different moisture contents are measured through tests based on the electromagnetic field distribution in the measurement field 1 of the ECT sensor, and a dielectric constant of the measurement field 1 of the ECT sensor in the finite element model of the ECT sensor is correspondingly changed to simulate a change of the electromagnetic field when the moisture content in the measurement field 1 of the ECT sensor changes, to realize an accurate analysis of the electromagnetic field when the moisture content in the concrete structure changes, thereby better explaining test results and providing a theoretical basis for a durability analysis of the concrete structure.

What is claimed is:

1. A method for optimizing a structure of an electrical capacitance tomography (ECT) sensor and analyzing an electromagnetic field, the method comprising steps of parameter setting, geometric setting, material setting, mesh generation, physical field setting, solution, sensor structure optimization and calculation of electromagnetic field distribution, wherein:

in parameter setting: sequentially inputting parameter values of components in a real diagram of the ECT sensor in a COMSOL software so as to change the parameter values quickly after modeling, and observing the electromagnetic field distribution in a measurement field of the ECT sensor when different design parameter values are given;

in geometric setting: establishing a finite element model of the ECT sensor according to the real diagram in the COMSOL software, and sequentially establishing a concrete component, a PVC layer, a copper electrode layer, a radial electrode layer, an air field, a shielding layer and an impurity region in the measurement field of the ECT sensor by taking a center of the finite element model of the ECT sensor as a center of a circle;

in material setting: setting a material of the measurement field of the ECT sensor as concrete, setting a material of the PVC layer as plastic, setting materials of the copper electrode layer and the shielding layer as copper, setting a material of the air field as air, and setting material properties of the impurity region according to setting requirements;

in mesh generation: setting a category of a mesh generation of a region of the finite element model of the ECT sensor as free triangular mesh generation, and setting sizes of maximum and minimum unit meshes according to set accuracy to further improve calculation accuracy;

in physical field setting: sequentially setting 12 electrodes of the finite element model of the ECT sensor as terminals, and setting parametric scanning so that electrode plates are excited in turn in a measurement process; observing the electromagnetic field distribution under different excitation conditions; and setting an external shielding device to be grounded;

in solution: calculating a Maxwell capacitance matrix, a mutual inductance capacitance matrix and a sensitivity matrix in the COMSOL software, and sequentially drawing detailed data diagrams of an electric field, potential and sensitivity, thereby preliminarily completing the calculation of the electromagnetic field distribution in the measurement field of the ECT sensor;

in sensor structure optimization: introducing an optimization function by utilizing the sensitivity obtained in the solution step, and obtaining a set of optimal parameter values through a factor rotation design test method or an orthogonal optimization design method, to realize parameter optimization of the sensor structure, improve uniformity of a sensitive field, and obtain an ECT sensor with an optimized structure; and in calculation of electromagnetic field distribution: measuring relative dielectric constants of a concrete structure with different moisture contents through tests based on the electromagnetic field distribution in the measurement field of the ECT sensor, and correspondingly changing a dielectric constant of the measurement field of the ECT sensor in the finite element model of the ECT sensor to simulate a change of the electromagnetic field when the moisture content in the measurement field of the ECT sensor changes to realize an accurate analysis of the electromagnetic field when the moisture content in the concrete structure changes, thereby better explaining test results and providing a theoretical basis for a durability analysis of the concrete structure.

2. The method for optimizing the structure of the ECT sensor and analyzing the electromagnetic field according to claim 1, wherein the finite element model of the ECT sensor is two-dimensional; the concrete component in the measurement field of the ECT sensor is a linear and isotropic medium; a measurement frequency is within a low frequency band; the measurement field of the ECT sensor is set as an electrostatic field; and options of two-dimension, electrostatic module and stable state research are sequentially selected in the COMSOL software.

* * * * *